(12) United States Patent
Suzuki

(10) Patent No.: US 9,456,112 B2
(45) Date of Patent: Sep. 27, 2016

(54) ENDOSCOPE SYSTEM

(71) Applicant: OLYMPUS CORPORATION, Tokyo (JP)

(72) Inventor: Tatsuhiko Suzuki, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/040,063

(22) Filed: Feb. 10, 2016

(65) Prior Publication Data
US 2016/0165102 A1 Jun. 9, 2016

Related U.S. Application Data

(63) Continuation of application No. PCT/JP2014/070344, filed on Aug. 1, 2014.

(30) Foreign Application Priority Data

Aug. 20, 2013 (JP) .................. 2013-170553

(51) Int. Cl.
| | |
|---|---|
| H04N 5/217 | (2011.01) |
| G02B 23/26 | (2006.01) |
| G06T 5/00 | (2006.01) |
| G06T 5/20 | (2006.01) |
| H04N 9/64 | (2006.01) |
| H04N 9/73 | (2006.01) |
| H04N 5/225 | (2006.01) |
| A61B 1/00 | (2006.01) |

(52) U.S. Cl.
CPC ............ *H04N 5/2173* (2013.01); *G02B 23/26* (2013.01); *G06T 5/002* (2013.01); *G06T 5/20* (2013.01); *H04N 5/217* (2013.01); *H04N 9/646* (2013.01); *H04N 9/73* (2013.01); *A61B 1/00009* (2013.01); *G06T 2207/10068* (2013.01); *H04N 5/2254* (2013.01); *H04N 2005/2255* (2013.01)

(58) Field of Classification Search
CPC ............................... H04N 5/217; G02B 23/36
See application file for complete search history.

(56) References Cited

U.S. PATENT DOCUMENTS

| | | | |
|---|---|---|---|
| 2002/0159728 A1 | 10/2002 | Kobayashi et al. | |
| 2012/0236182 A1* | 9/2012 | Shintani ................ | G03B 17/14 348/240.3 |
| 2015/0371613 A1* | 12/2015 | Patel ....................... | G06F 21/10 345/549 |

FOREIGN PATENT DOCUMENTS

| | | |
|---|---|---|
| JP | 2001-070240 A | 3/2001 |
| JP | 2002-328311 A | 11/2002 |

(Continued)

OTHER PUBLICATIONS

International Search Report dated Nov. 4, 2014 issued in PCT/JP2014/070344.

(Continued)

*Primary Examiner* — Mehrdad Dastouri
*Assistant Examiner* — Joseph Becker
(74) *Attorney, Agent, or Firm* — Scully, Scott, Murphy & Presser, P.C.

(57) ABSTRACT

An endoscope system including: an optical endoscope including a fiber bundle that transmits an optical image; a camera head including an image pickup device; and a video processor including a moiré elimination section, a control section and an enhancement processing section, in which the moiré elimination section uses a processing circuit of the enhancement processing section as a processing circuit of itself by replacing a filter coefficient, the camera head includes a first identifier, the video processor includes a detection section that detects the first identifier, and the control section causes the moiré elimination section to perform moiré elimination processing corresponding to a detection result of the first identifier.

5 Claims, 9 Drawing Sheets

(56) References Cited

FOREIGN PATENT DOCUMENTS

| | | |
|---|---|---|
| JP | 2006-254974 A | 9/2006 |
| JP | 2010-193093 A | 9/2010 |

OTHER PUBLICATIONS

Japanese Office Action dated Jun. 3, 2015 issued in JP 2015-511844.

\* cited by examiner

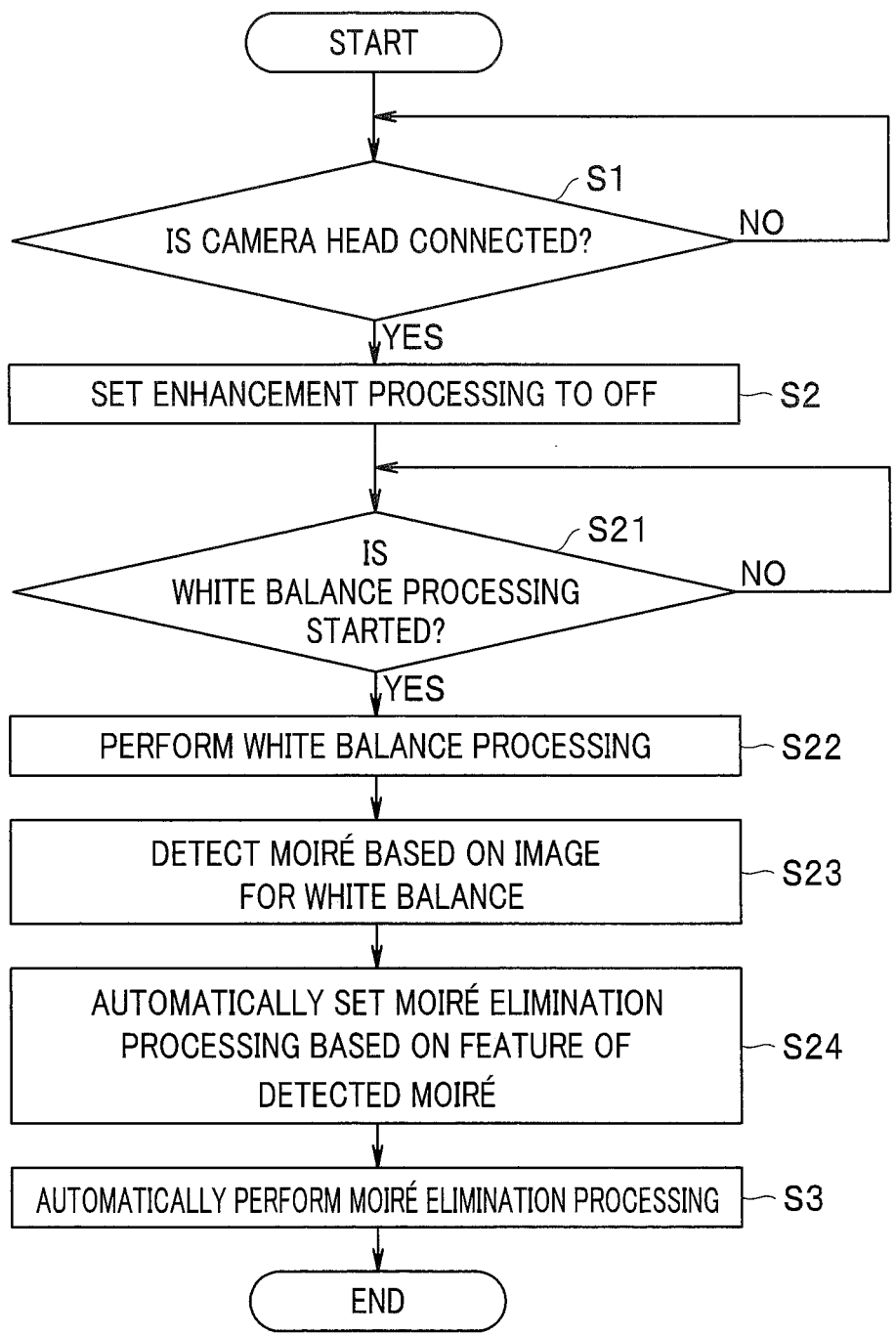

ENDOSCOPE SYSTEM

CROSS REFERENCE TO RELATED APPLICATION

This application is a continuation application of PCT/JP2014/070344 filed on Aug. 1, 2014 and claims benefit of Japanese Application No. 2013-170553 filed in Japan on Aug. 20, 2013, the entire contents of which are incorporated herein by this reference.

BACKGROUND OF THE INVENTION

1. Field of the Invention

The present invention relates to an endoscope system that picks up an optical image, which is transmitted by an image guide fiber bundle, by an image pickup device.

2. Description of the Related Art

A video processor that processes video signals obtained from an endoscope is configured to be connected with various kinds of endoscope image pickup apparatuses, if the standards of the endoscope image pickup apparatuses match with the standard of the processor. Such a video processor is connected with what is called a video scope in some cases, and connected with a camera head attached to an eye piece of an optical endoscope in other cases.

Specifically, Japanese Patent Application Laid-Open Publication No. 2001-70240 discloses a technique for enabling endoscope image pickup apparatuses for various purposes of use to be connected with a common video processor. The publication recites, for example, an endoscope image pickup apparatus in which an image pickup apparatus that picks up an image of an object and obtains a video signal is detachably connected to an endoscope that obtains an image of an object as an optical image.

The optical endoscope that obtains the optical image of the object has a structure for transmitting the optical image obtained from the distal end portion of the insertion portion to the rear end portion of the insertion portion by an image guide, and when the optical endoscope is a fiber scope, for example, a fiber bundle configured by binding a plurality of optical fibers is used as an image guide.

When a camera head is connected to an eye piece of such a fiber scope to perform video observation through a video processor and a monitor, a moiré fringe pattern is sometimes generated by an interference between the mesh pattern of the fiber bundle (mesh pattern generated by binding the optical fibers) and the pixels of the image pickup device of the camera head. In addition, the same is true on a hybrid scope, i.e., a scope of a type in which an optical image is transmitted from the distal end to the proximal end of the insertion portion by a fiber bundle and the transmitted optical image is picked up by an image pickup device provided at the proximal end portion of the insertion portion.

In order to address such a case, conventionally, observation has been performed at a focus position at which moiré is not distinct by shifting the focus of the optical system or observation has been performed by turning off the enhancing function in the video processor by manual operation in order to prevent the moiré from being enhanced.

SUMMARY OF THE INVENTION

An endoscope system according to an aspect of the present invention including: an optical endoscope including an insertion portion configured to be inserted into a subject, an objective optical system provided at a distal end portion of the insertion portion, and an image guide fiber bundle that transmits an optical image formed by the objective optical system from the distal end portion to a rear end portion of the insertion portion; a camera head configured to be attachable to and detachable from the optical endoscope and including an image pickup device that picks up the optical image transmitted by the image guide fiber bundle and generates a video signal; a video signal output section that is provided in the camera head and outputs the video signal generated by the image pickup device; a video processor that is configured such that the camera head is attachable to and detachable from, and processes the video signal; a video signal reception section that is provided in the video processor and receives the video signal outputted from the video signal output section; a moire elimination section that is provided in the video processor and performs moire elimination processing for eliminating moiré included in the video signal received by the video signal reception section, by means of image processing; a control section that is provided in the video processor and causes the moiré elimination section to perform the moiré elimination processing; and an enhancement processing section that is provided in the video processor and performs image enhancement on the video signal, wherein the moiré elimination section is configured as a result that a filter coefficient to be used when the enhancement processing section performs image enhancement is replaced with a filter coefficient for moiré elimination, and the moiré elimination section uses a processing circuit of the enhancement processing section as a processing circuit of the moiré elimination section itself, the camera head further includes a first identifier for identifying a type of the camera head, the video processor includes a first identifier detection section that detects the first identifier of the camera head connected to the video processor, and the control section causes the moiré elimination section to perform the moiré elimination processing corresponding to a detection result of the first identifier.

BRIEF DESCRIPTION OF THE DRAWINGS

FIG. 11 is a flowchart showing a working of the endoscope system according to the fourth embodiment.

DETAILED DESCRIPTION OF THE PREFERRED EMBODIMENTS

Hereinafter, embodiments of the present invention will be described with reference to drawings.

First Embodiment

Figure 1:
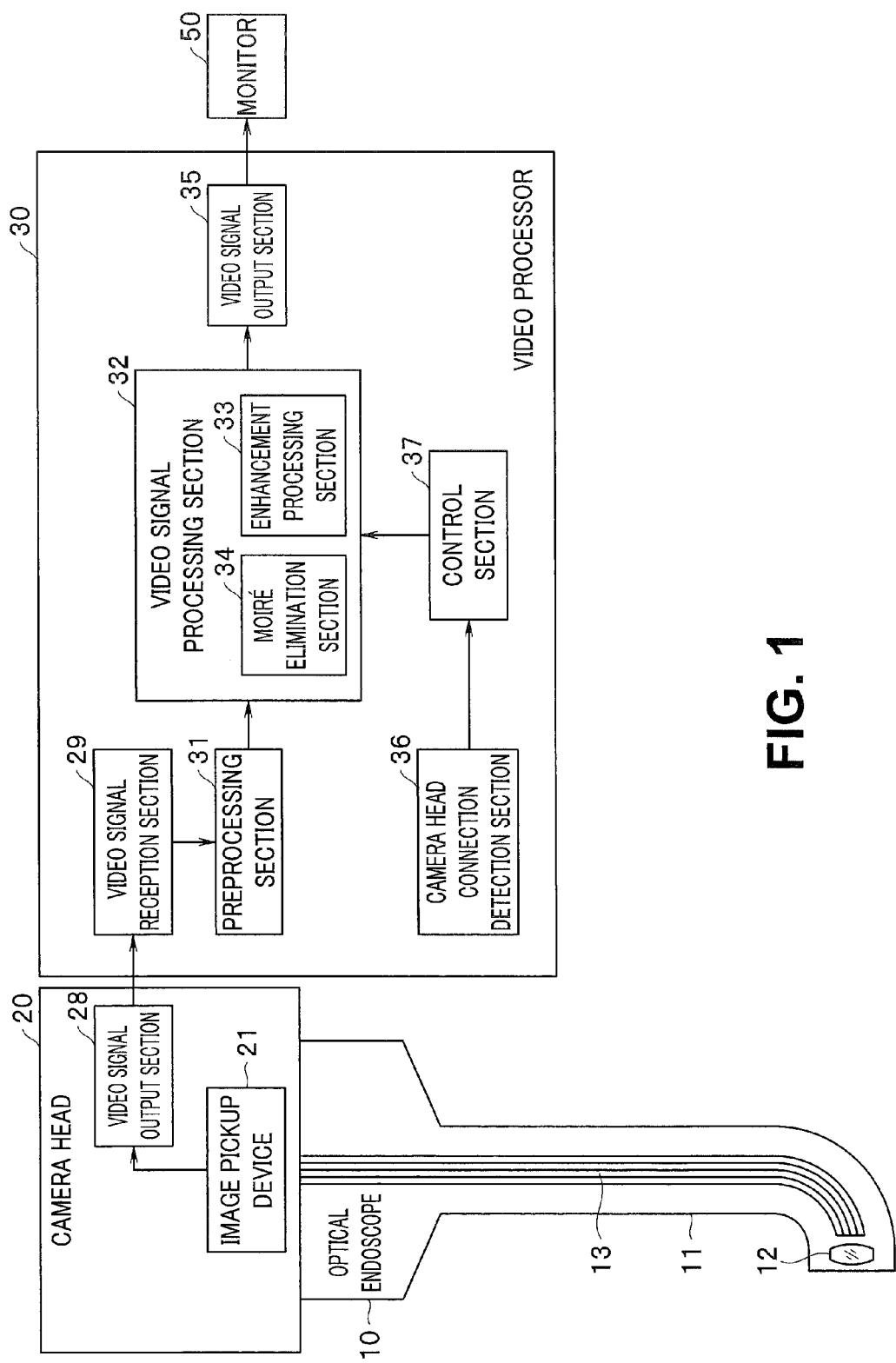
FIG. 1 is a block diagram showing a configuration of an endoscope system according to a first embodiment of the present invention.

FIGS. 1 to 5 illustrate the first embodiment of the present invention, and FIG. 1 is a block diagram showing a configuration of an endoscope system.

As shown in FIG. 1, an endoscope system according to the present embodiment includes an optical endoscope 10, a camera head 20, a video processor 30, and a monitor 50.

The optical endoscope 10 includes an insertion portion 11 configured to be inserted into a subject, an objective optical system 12 provided at a distal end portion of the insertion portion 11, and an image guide fiber bundle 13 that transmits an optical image of an object, which has been formed by the objective optical system 12, from the distal end portion to a rear end portion of the insertion portion 11, and the optical endoscope 10 is configured as what is called a fiber scope.

Figure 2:
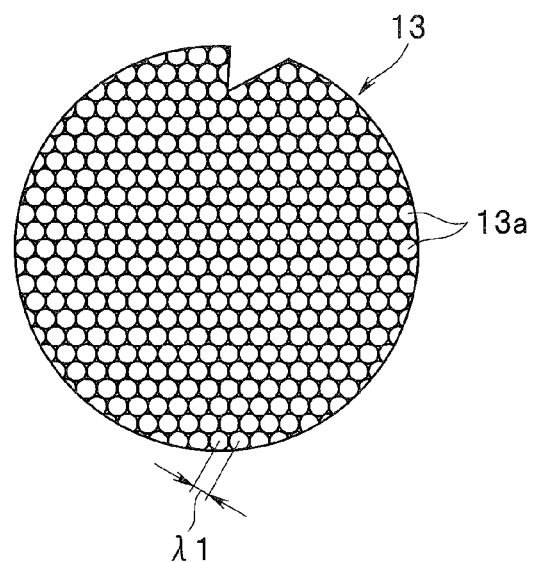
FIG. 2 is an end view showing an exemplary configuration of an image guide fiber bundle according to the first embodiment.

FIG. 2 is an end view showing an exemplary configuration of the image guide fiber bundle 13. The image guide fiber bundle 13 is configured by binding a plurality of small-diameter optical fibers 13a. Each of the optical fibers 13a has a circular cross section, and the densest arrangement of the optical fibers (arrangement in which the number of optical fibers becomes the largest per unit area) is achieved by a hexagonal lattice arrangement. The hexagonal lattice has different arrangement pitches, depending on in which direction measurement of the arrangement pitches is made. One of the arrangement pitches in such a hexagonal lattice arrangement is, for example, represented by $\lambda 1$ shown in FIG. 2.

The camera head 20 is configured to be attachable to and detachable from the optical endoscope 10, and includes an image pickup device 21 that picks up an optical image transmitted by the image guide fiber bundle 13, to generate a video signal, and a video signal output section 28 that outputs the video signal generated by the image pickup device 21.

Figure 3:
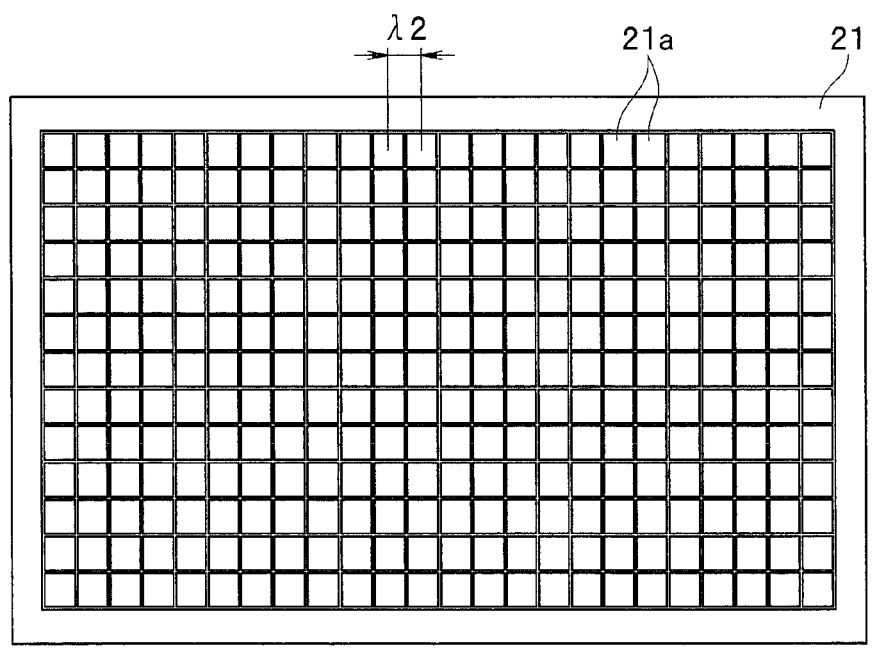
FIG. 3 is a front view showing an example of a pixel composition of an image pickup device according to the first embodiment.

FIG. 3 is a front view showing an example of a pixel composition of the image pickup device 21. The image pickup device 21 is configured by a plurality of pixels 21a being arranged in a tetragonal lattice (that is, row direction and column direction), for example. When the tetragonal lattice is a rectangular lattice other than a square lattice, the arrangement pitches (pixel pitches) of the pixels 21a differ in the row direction and in the column direction. One of the arrangement pitches in such a case is represented by $\lambda 2$ shown in FIG. 3, for example. Note that the arrangement pitch $\lambda 2$ can be calculated based on the size of the image pickup surface and the number of horizontal and vertical pixels of the image pickup device 21.

Figure 4:
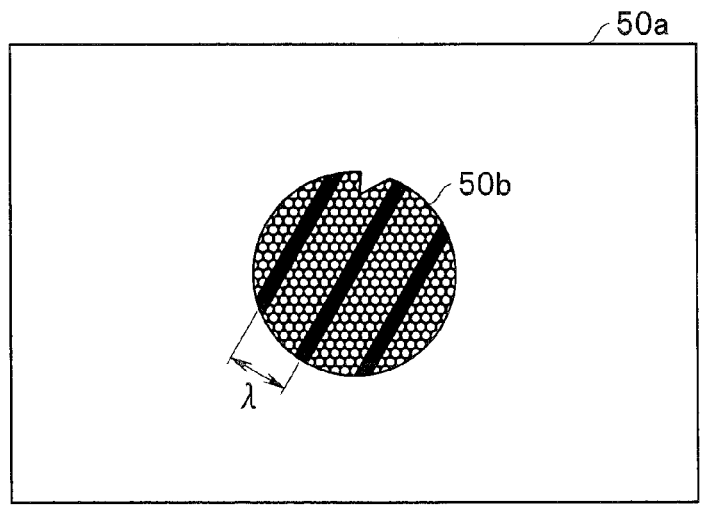
FIG. 4 illustrates an example of an image picked up by the image pickup device through the image guide fiber bundle in the first embodiment.

When the optical image transmitted by the image guide fiber bundle 13 as shown in FIG. 2 is picked up by the image pickup device 21 having the pixel composition as shown in FIG. 3, moiré, as interference fringes, is generated due to misalignment between the arrangement pattern of the optical fibers 13a and the arrangement pattern of the pixels 21a, and a display image 50b in which the moiré as shown in FIG. 4 is generated is sometimes observed on a monitor screen 50a. FIG. 4 illustrates an example of the image picked up by the image pickup device 21, through the image guide fiber bundle 13. In the example shown in FIG. 4, the arrangement pitch of the moiré is represented by $\lambda$, for example.

The video processor 30 to which the camera head 20 is detachably connected is configured to process video signals. The video processor 30 includes a video signal reception section 29, a preprocessing section 31, a video signal processing section 32, a video signal output section 35, a camera head connection detection section 36, and a control section 37.

The video signal reception section 29 receives the video signal outputted from the video signal output section 28.

The preprocessing section 31 performs processing such as amplification of the video signal received by the video signal reception section 29, elimination of noise, and conversion from an analog signal to a digital signal.

The video signal processing section 32 performs various kinds of video signal processing on the video signal from the preprocessing section 31, and includes an enhancement processing section 33, and a moiré elimination section 34.

The enhancement processing section 33 performs image enhancement processing on the video signal. Specifically, the enhancement processing section 33 performs a filter operation (for example, matrix operation) on a pixel block, which is constituted of n×m pixels (n and m are positive integers) centering on a pixel of interest, by an enhancement filter (for example, enhancement filter coefficient matrix), to calculate processing result of the pixel of interest. The enhancement processing section 33 performs the operation on all of the pixels while shifting the position of the pixel of interest one by one, to obtain an image subjected to the enhancement processing.

The moiré elimination section 34 performs processing of eliminating (this "eliminating" includes a case where the moiré is eliminated completely and a case where the moiré cannot be eliminated completely but is eliminated to some extent) the moiré included in the video signal, as shown in FIG. 4, by means of image processing. For example, the moiré elimination section 34 performs processing (filtering processing, for example) having a characteristic in which the arrangement pitch $\lambda$ (wavelength of the moiré) as shown in FIG. 4 is included in an elimination band (band in which the signal value is reduced). One example of a moiré elimination filter for performing such moiré elimination processing is a Gaussian Filter, but other filters (for example, a smoothing filter, etc.) may be used. The moiré elimination processing is also performed in a similar manner as the above-described enhancement processing, by performing the moiré elimination filter operation on all of the pixels, while shifting the position of the pixel of interest one by one, for example.

The video signal processing section 32 further performs general video signal processing such as white balance processing, color space conversion, and gradation conversion including gamma conversion.

The video signal output section 35 outputs the video signal processed by the video signal processing section 32 to the monitor 50.

The camera head connection detection section 36 is a connection detection section configured to detect that the video signal output section 28 is connected to the video processor 30. The connection to be detected by the connection detection section may be a wired connection or a wireless connection. The camera head connection detection section 36 according to the present embodiment, in particular, is configured to detect that the camera head 20 is connected to the video processor 30 (that is, detect that the apparatus connected to the video processor 30 is not another apparatus such as a video scope but the camera head 20). As a connection detecting method of the camera head 20 by the camera head connection detection section 36, a method which will be described in an embodiment to be described later can be considered. For example, it is a method of providing a first identifier 22 (see FIG. 6, etc.) in the camera head 20 and detecting the information from the first identifier 22 by the camera head connection detection section 36. When the first identifier 22 is configured by a storing section that stores the model number of the camera head 20, for example, the camera head connection detection section 36 has only to be configured to read the model number from the storing section. Alternatively, when the first identifier 22 is configured by a resistor element (resistor element having a resistance value corresponding to the type of the camera head 20) connected to the ground of the camera head 20, for example, the camera head connection detection section 36 may determine the type of the camera head 20, based on a digital value obtained by pulling up voltage in the video processor 30 and performing A/D conversion on voltage determined by the voltage division ratio. Furthermore, an identification code such as a bar code or a QR code (Registered Trademark) corresponding to the type of the camera head 20 is printed on the surface of the camera head 20, and the camera head connection detection section 36 may be configured to optically read the identification code. Or when the surface color of the camera head 20 is made greatly different from the surface color of the video scope or the like, and the surface color of the camera head 20 is made slightly different for each type of the camera head 20, for example, the camera head connection detection section 36 can be configured by a color detection element, or the like, to determine the type of the camera head 20 based on the color.

Thus, any method may be used for the connection detection of the camera head 20 by the camera head connection detection section 36, and a specific first identifier 22 is not necessarily required. Therefore, the first identifier 22 is not shown in FIG. 1 according to the present embodiment.

The control section 37 controls the entirety of the video processor 30, or the entirety of the endoscope system including the camera head 20 and the monitor 50 (or further including the optical endoscope 10).

The monitor 50 is a display section (or a display apparatus) that displays the endoscopic image based on the video signal processed by the video processor 30, various kinds of information related to the endoscope system, and the like.

Figure 5:
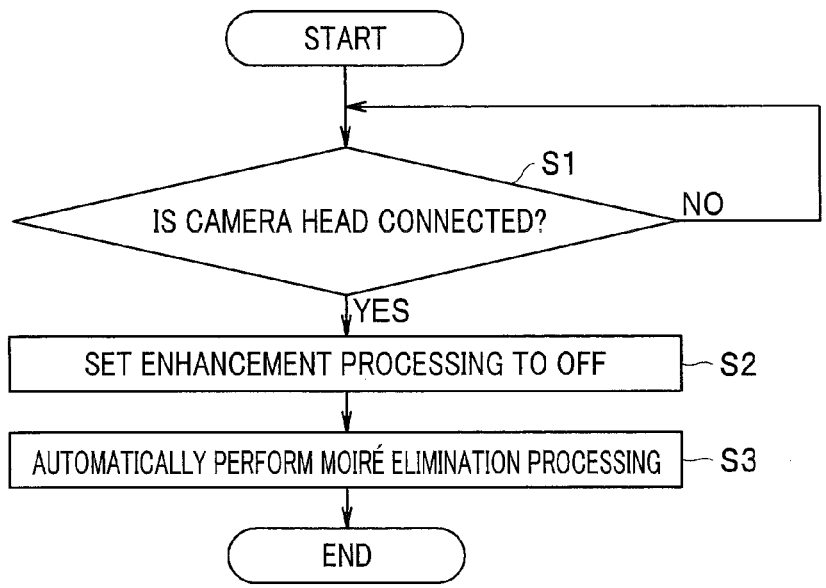
FIG. 5 is a flowchart showing a working of the endoscope system according to the first embodiment.

Next, FIG. 5 is a flowchart showing the working of the endoscope system. Note that the processing steps shown in FIG. 5 are performed based on the control by the control section 37. In addition, in FIG. 5, illustration of control other than the control related to the enhancement processing and the moiré elimination processing is omitted for simplification.

Upon starting the processing procedure, the control section 37 monitors the detection result obtained by the camera head connection detection section 36, to wait for detection of the connection of the camera head 20 (step S1).

When the connection of the camera head 20 is detected, the control section 37 controls the video signal processing section 32 to set the enhancement processing by the enhancement processing section 33 to off (step S2), and then causes the moiré elimination section 34 to perform the moiré elimination processing (step S3), to terminate the processing procedure.

According to the first embodiment thus configured, when the connection of the camera head 20 is detected, the enhancement processing is automatically set to off. This eliminates the need for manually setting the enhancement processing to off, which leads to simple operation. As a result, operability can be improved.

Furthermore, when the connection of the camera head 20 is detected, the moiré elimination processing is automatically performed, to thereby enable a high-quality image in which the moiré is eliminated to be observed. In addition, manual defocus adjustment, etc., are not required, which further improves the operability.

Thus, when the optical image transmitted by the image guide fiber bundle 13 is picked up with the camera head 20 having the image pickup device 21, the image in which the moiré is eliminated can be observed without a cumbersome operation.

Second Embodiment

Figure 6:
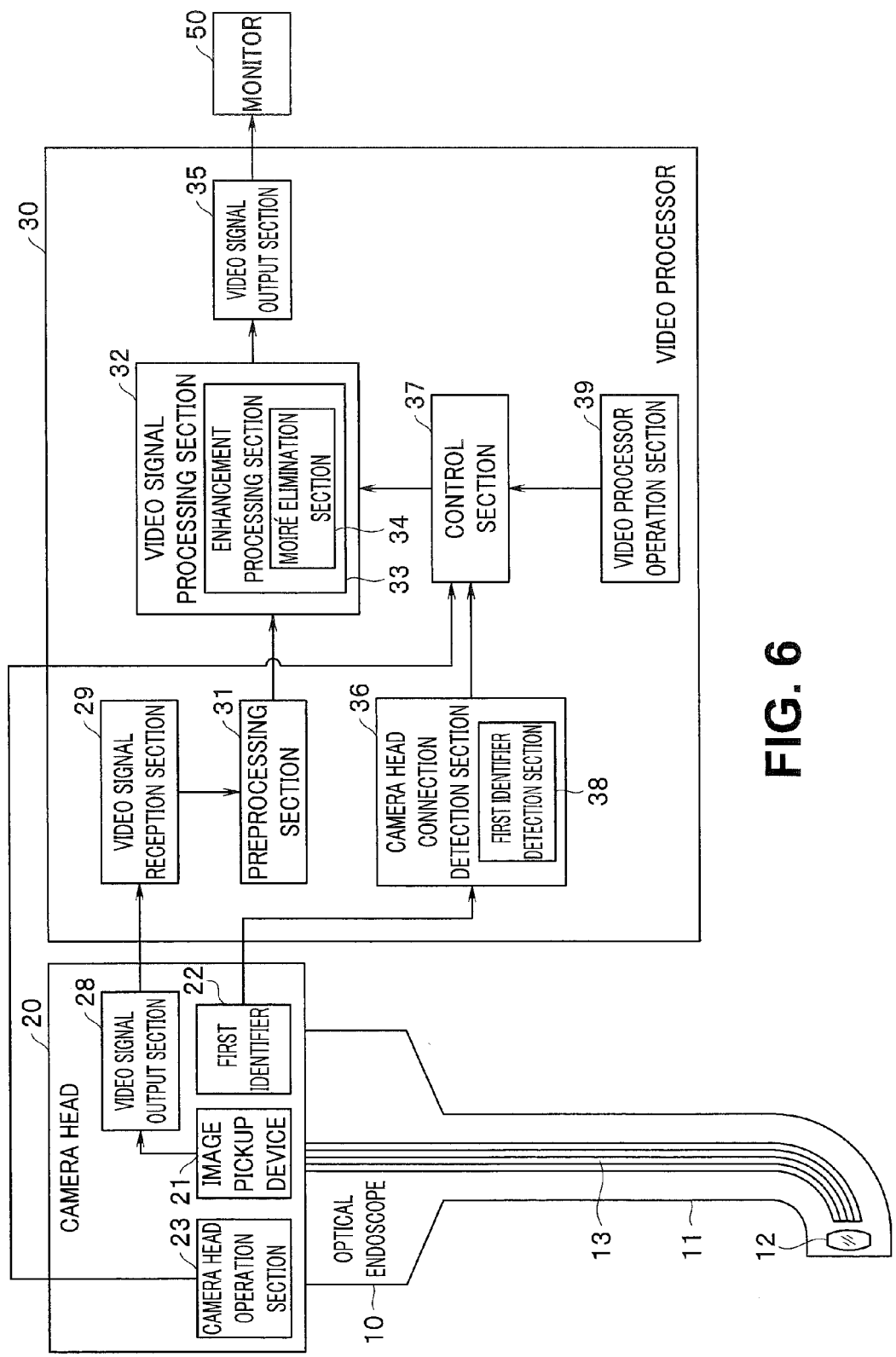
FIG. 6 is a block diagram showing a configuration of an endoscope system according to a second embodiment of the present invention.
Figure 7:
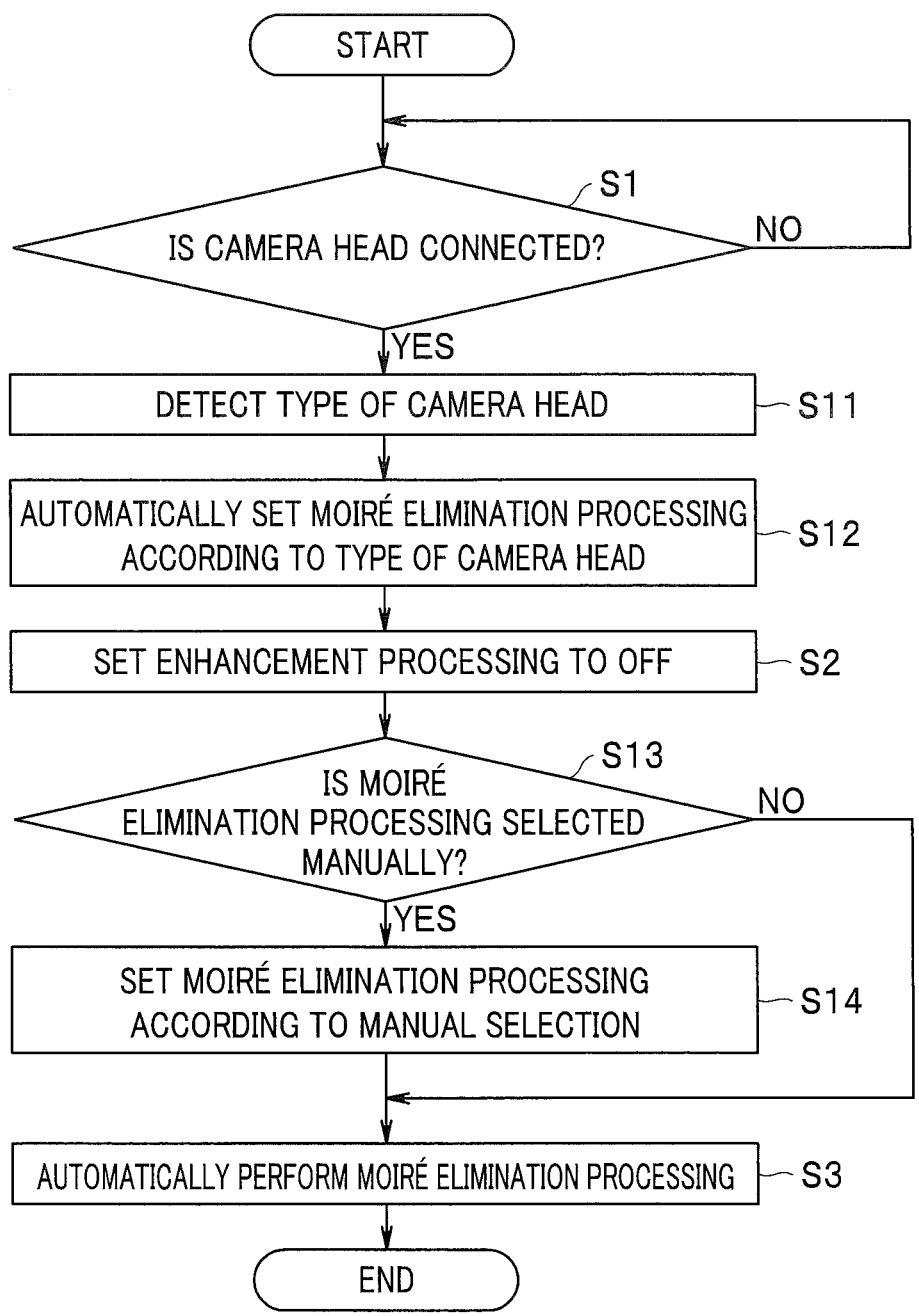
FIG. 7 is a flowchart showing a working of the endoscope system according to the second embodiment.

FIGS. 6 and 7 show the second embodiment of the present invention, and FIG. 6 is a block diagram showing a configuration of an endoscope system. In the second embodiment, the parts same as those in the first embodiment are attached with the same reference numerals, to appropriately omit the description thereof, and mainly, description will be made on only different points.

In the present embodiment, not only the presence or absence of connection of the camera head 20 but also the type of the camera head 20 is detected based on the first identifier 22 provided in the camera head 20.

That is, the camera head 20 includes the above-described image pickup device 21, the above-described video signal output section 28, the first identifier 22, and a camera head operation section 23 as an operation section.

The first identifier 22, as described above, indicates that the device including the first identifier 22 is the camera head 20 and is not a device such as a video scope other than the camera head 20, (accordingly, hereinafter identification information provided in a device other than the camera head 20 will not be called as the first identifier 22), and the first identifier 22 is used for identifying the type of the camera head 20. A specific example of the first identifier 22 is a storing section (ROM, for example) that stores the information related to the type (for example, model number (this model number is eventually the information indicating the pixel pitch of the image pickup device 21), etc.) of the camera head 20 in a non-volatile manner.

The camera head operation section 23 performs input operation in the camera head 20, and is capable of performing operation for selecting desired moiré elimination processing from among a plurality of moiré elimination processings each having different moiré elimination capability, for example (this moiré elimination capability varies depending on how the center band and the band width of the elimination band are set with respect to the wavelength of the moiré, or how the reduction level of the signal value in the elimination band is set with respect to the intensity of the moiré). The operation input from the camera head operation section 23 is connected to the control section 37 of the video processor 30.

On the other hand, the video processor 30 further includes a video processor operation section 39 as an operation section, and is configured such that the enhancement processing section 33 in the video signal processing section 32 also serves as the moiré elimination section 34, and the camera head connection detection section 36 includes a first identifier detection section 38. In the present embodiment, when the existence of the first identifier 22 is detected, the camera head connection detection section 36 outputs the detection result that the camera head 20 has been detected.

The filtering processing to be performed by the moiré elimination section 34 differs from the filtering processing to be performed by the enhancement processing section 33 only in the filter coefficient. Both of the processings are able to be performed by the same processing circuit. Therefore, the enhancement processing section 33 and the moiré elimination section 34 are configured to use the same processing circuit, and the moiré elimination section 34 is configured as a result that the filter coefficient to be used when the enhancement processing section 33 performs image enhancement is replaced with the filter coefficient for moiré elimination.

In addition, connection of the camera head 20 to the video processor 30 allows the first identifier 22 to be connected to the camera head connection detection section 36. The first identifier detection section 38 provided in the camera head connection detection section 36 detects the first identifier 22 to read the information such as the model number, and the like. Thus, the presence or absence of the connection of the camera head 20 is determined based on the existence or non-existence of the first identifier 22, and the type of the camera head 20 is determined based on the information read from the first identifier 22.

The video processor operation section 39 performs input operation in the video processor 30, and is capable of selecting desired moiré elimination processing from among a plurality of moiré elimination processings each having different moire elimination capability, for example, similarly as the camera head operation section 23. The operation input from the video processor operation section 39 is connected to the control section 37.

Next, FIG. 7 is a flowchart showing the working of the endoscope system. Note that the processing steps shown in FIG. 7 are performed based on the control by the control section 37. In addition, in FIG. 7, illustration of control other than the control related to the enhancement processing and the moiré elimination processing is omitted for simplification.

Upon starting the processing procedure, the control section 37 performs the processing in the above-described step S1, to wait for the connection of the camera head 20. When detecting the connection, the control section 37 detects the type of the camera head 20 based on the detection result by the first identifier detection section 38 (step S11).

Then, according to the detected type of the camera head 20, the control section 37 automatically sets, for the moiré elimination section 34, moiré elimination processing with which moiré can be effectively eliminated (step S12).

Specifically, a plurality of kinds of moiré elimination filters each having a different center band and a band width of the moiré elimination band and a different reduction level of the signal value in the moiré elimination band (for practical purposes, each filter has a different filter coefficient) are prepared in advance in the moire elimination section 34. The control section 37 is configured to select a moire elimination filter that effectively eliminates the feature of the moiré which is estimated to occur according to the type of the camera head 20 (for example, the moire elimination filter having the center band of the moiré elimination band which is closest to the estimated wavelength of the moiré, having the moiré elimination band in which all the wavelengths, if possible, are included when moiré having a plurality of wavelengths occurs, and having a reducing level of the signal value which corresponds to the intensity of the moiré), and set the selected moiré elimination filter for the moire elimination section 34.

However, for the practical purposes, it can be considered that the control section 37 previously includes a table or the like that indicates which moiré elimination filter is applied to which type of the camera head 20, and sets the moiré elimination filter with reference to the table.

Next, the control section 37 performs the processing in the above-described step S2 to set the enhancement processing to off, and thereafter determines whether or not the operation of manually selecting desired moiré elimination processing has been performed through the camera head operation section 23 or the video processor operation section 39 (step S13).

When the manual selection operation has been performed, the control section prioritizes the manually selected moiré elimination processing over the moire elimination processing automatically set in the step S12, to set the prioritized moire elimination processing for moiré elimination section 34 (step S14).

After that, in the step S3, the control section 37 causes the moiré elimination section 34 to perform the moiré elimination processing according to the manually set moiré elimination processing, when having performed the processing in the step S14, and to perform the moiré elimination processing according to the automatically set moiré elimination processing in the step S12, when the manual section operation is not performed in the step S13, and then terminates the processing procedure.

According to the second embodiment thus configured, it is possible to provide almost the same effects as those in the above-described first embodiment. In addition, the moiré elimination processing corresponding to the type of the camera head 20 is performed based on the detection result of the first identifier 22 in the second embodiment, which enables the moiré to be eliminated more effectively.

In addition, the present embodiment allows the moiré elimination processing to be manually selected, which enables the user to select a desired moiré elimination degree and an image sharpness, which are in a trade-off relationship, while checking the monitor 50.

Furthermore, the moiré elimination section 34 and the enhancement processing section 33 are configured to use the one processing circuit, which simplifies the configuration and enables the manufacturing cost to be effectively reduced.

Third Embodiment

Figure 8:
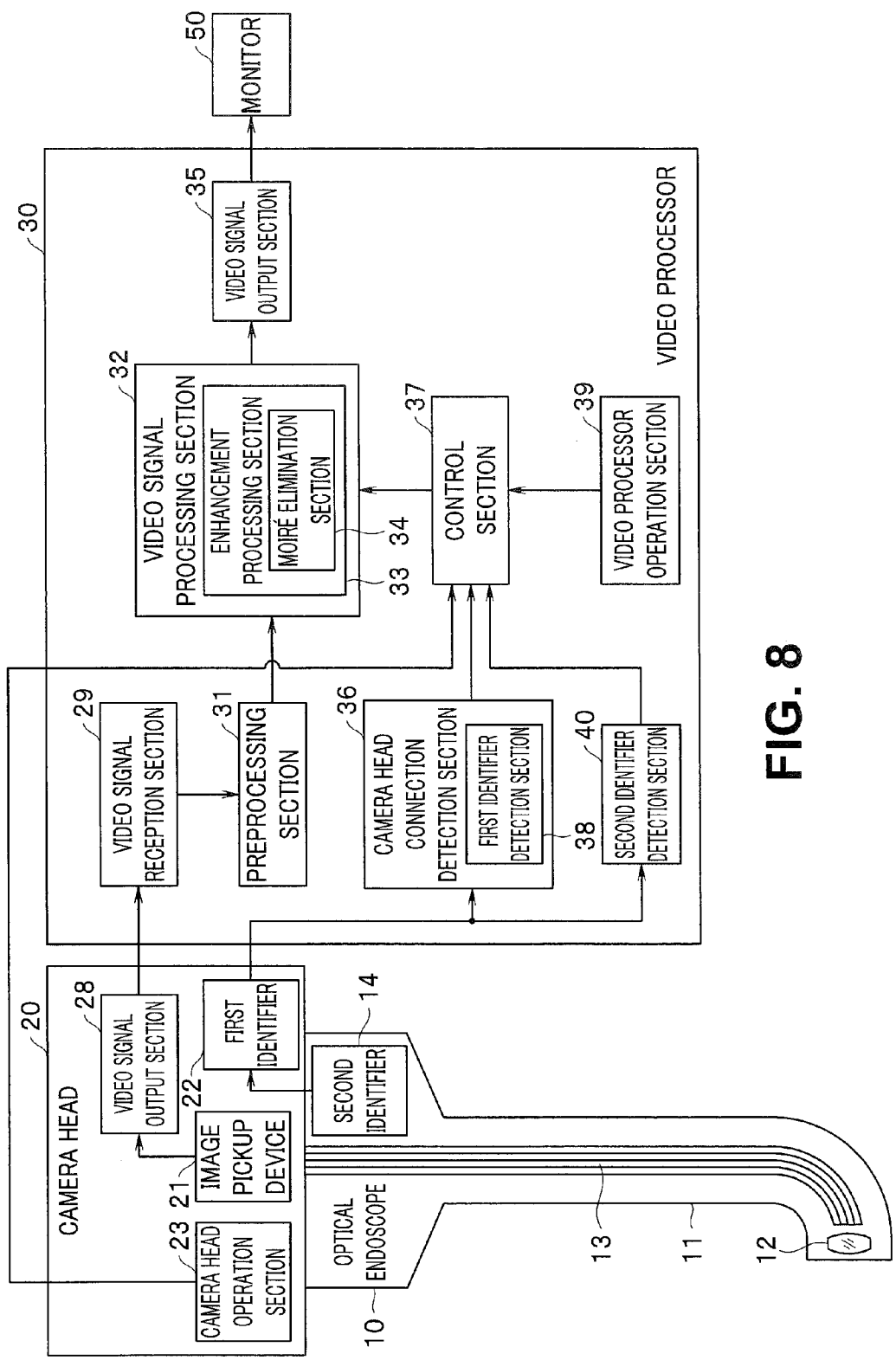
FIG. 8 is a block diagram showing a configuration of an endoscope system according to a third embodiment of the present invention.
Figure 9:
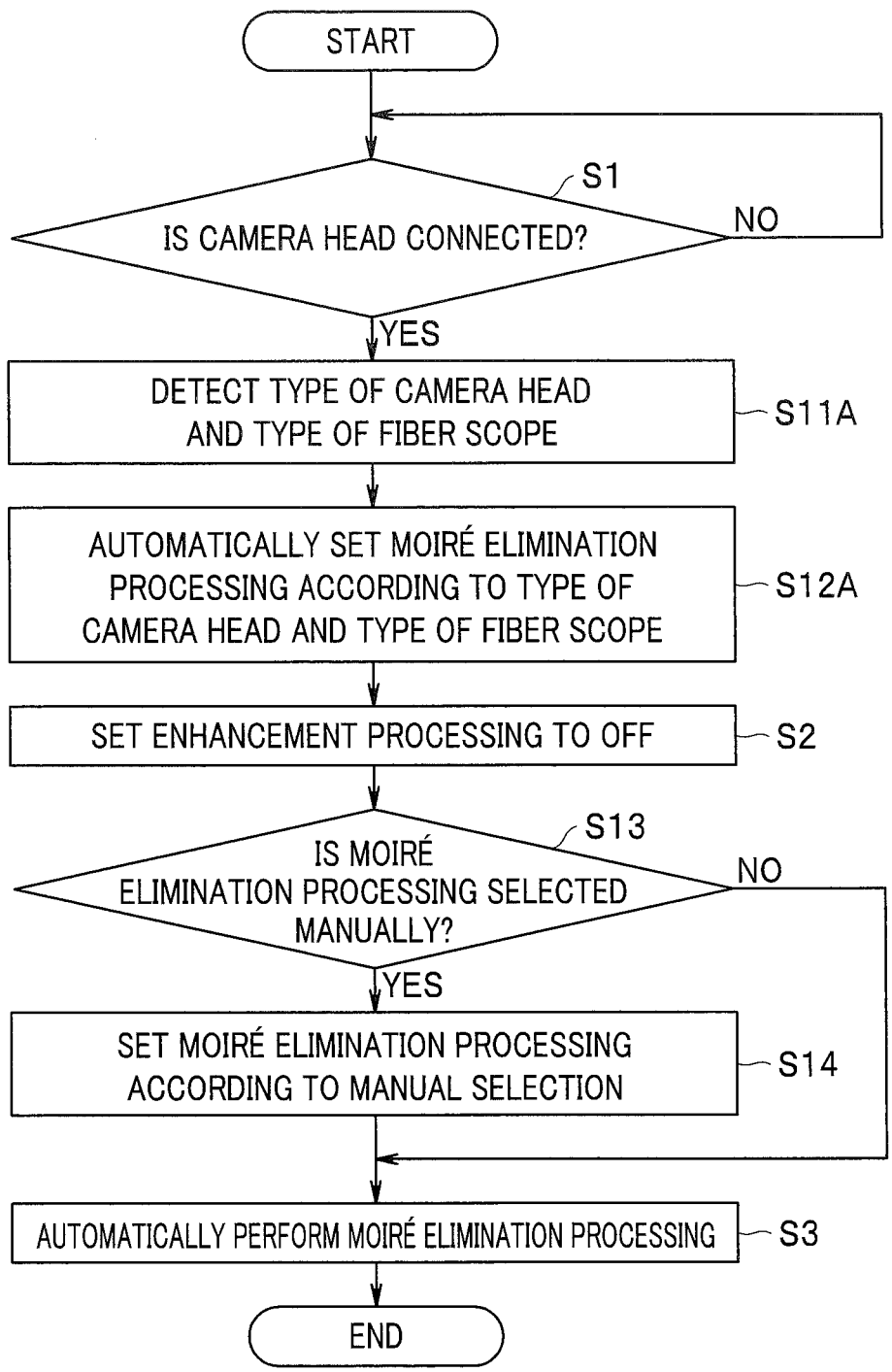
FIG. 9 is a flowchart showing a working of the endoscope system according to the third embodiment.

FIGS. 8 and 9 show the third embodiment of the present invention, and FIG. 8 is a block diagram showing the configuration of the endoscope system. In the third embodiment, the parts same as those in the first and second embodiments are attached with the same reference numerals, to appropriately omit the description thereof, and mainly, description will be made only on different points.

The present embodiment is configured to detect the presence or absence of the connection and the type of the camera head 20, and the type of the optical endoscope 10, based not only on the first identifier 22 provided in the camera head 20 but also on a second identifier 14 provided in the optical endoscope 10.

That is, the optical endoscope 10 further includes the second identifier 14 in addition to the above-described configuration in the first embodiment. The second identifier 14 is used for identifying the type of the optical endoscope 10, and one specific example of the second identifier is a storing section (for example, nonvolatile memory such as ROM) that stores information on the type of the optical endoscope 10 (for example, the model number (the model number is eventually the information indicating the diameter of the optical fibers 13a of the image guide fiber bundle 13) in a non-volatile manner.

The second identifier 14 is connected to the video processor 30 through the first identifier 22, for example, (in this regard, however, not necessarily through the first identifier 22).

The video processor 30 further includes a second identifier detection section 40 for detecting the second identifier 14, in addition to the above-described configuration in the second embodiment. The second identifier detection section 40 detects the second identifier 14, to read the information (model number, etc.) on the type of the optical endoscope 10.

Next, FIG. 9 is a flowchart showing the working of the endoscope system. Note that the processing steps shown in FIG. 9 are performed based on the control by the control section 37. In addition, in FIG. 9, illustration of control other than the control related to the enhancement processing and the moiré elimination processing is omitted for simplification.

Upon starting the processing procedure, the control section 37 performs the processing in the above-described step S1, to wait for the connection of the camera head 20. When detecting the connection, the control section 37 detects the type of the camera head 20 and the type of the optical endoscope 10, based on the detection result by the first identifier detection section 38 and the detection result by the second identifier detection section 40 (step S11A).

Then, according to the detected type of the camera head 20 and the detected type of the optical endoscope 10, the control section 37 automatically sets, for the moiré elimination section 34, the moiré elimination processing with which moiré can be effectively eliminated (step S12A).

After that, the control section performs the processing in the step S2 and subsequent steps shown in FIG. 7 according to the second embodiment, to terminate the processing procedure.

According to the third embodiment thus configured, it is possible to provide almost the same effects as those in the above-described first and second embodiments. In addition, selection of the moiré elimination processing is performed according to the detection result of the first identifier 22 and the detection result of the second identifier 14, that is, according to not only the type of the camera head 20 but also the type of the optical endoscope 10 in the third embodiment, which enables the moiré to be eliminated more efficiently.

Fourth Embodiment

Figure 10:
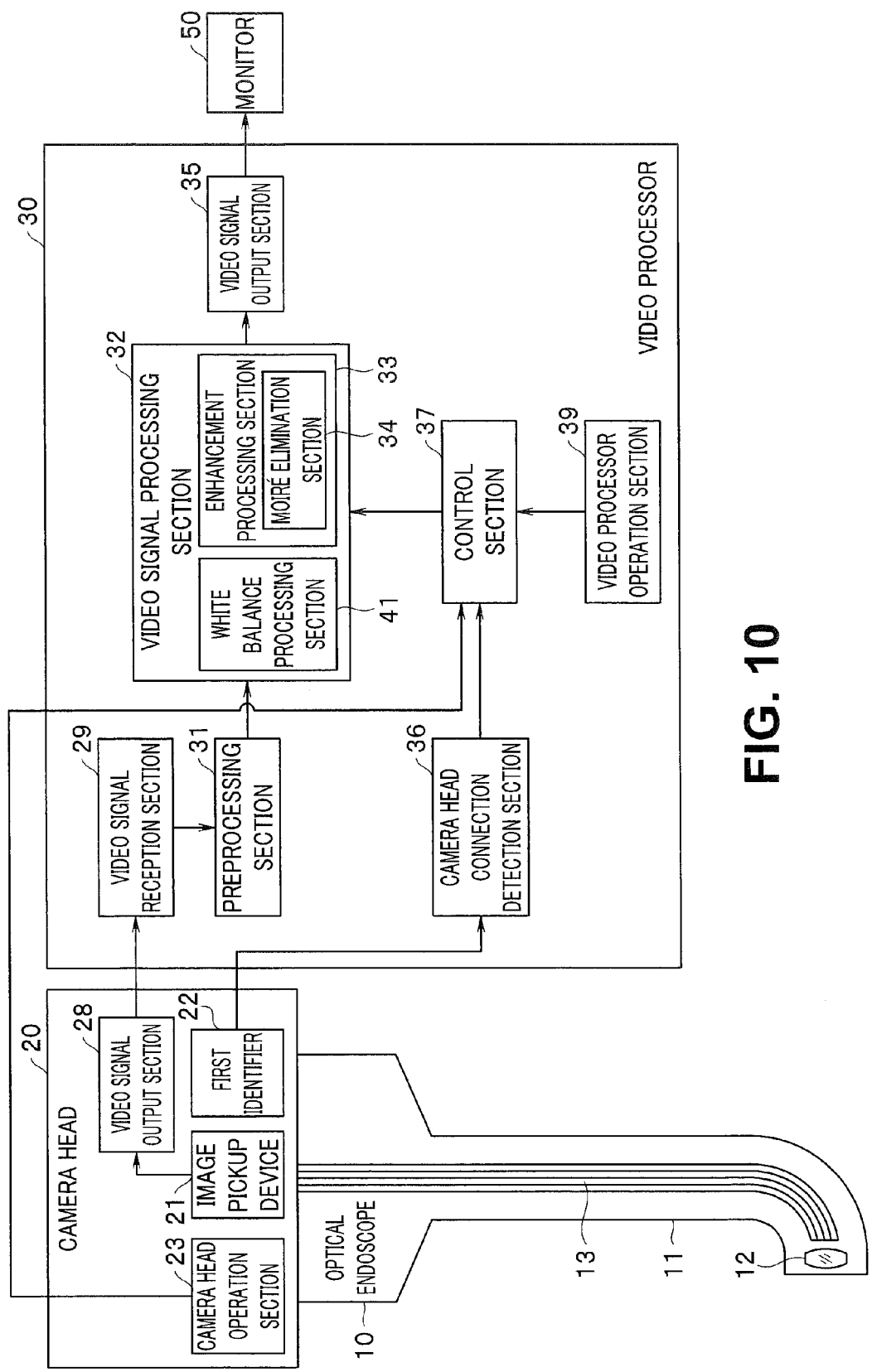
FIG. 10 is a block diagram showing a configuration of an endoscope system according to a fourth embodiment of the present invention.

FIGS. 10 and 11 show the fourth embodiment of the present invention, and FIG. 10 is a block diagram showing the configuration of the endoscope system. In the fourth embodiment, the parts same as those in the first to third embodiments are attached with the same reference numerals, to appropriately omit the description thereof, and mainly, description will be made only on different points.

The moiré elimination processing is performed according to the type of the camera head 20 in the second embodiment, and performed according to the types of the camera head 20 and the optical endoscope 10 in the third embodiment. In the present embodiment, moiré is directly detected from a video signal and moiré elimination processing is performed according to the detected moiré.

In the above-described embodiments, description has been made that the video signal processing section 32 performs white balance processing as common video signal processing. In the present embodiment, in order to make a description on an example in which the white balance processing is used in association with the moiré elimination processing, a white balance processing section 41 is illustrated in the video signal processing section 32. At least one of the camera head operation section 23 and the video processor operation section 39 is capable of performing an operation for starting the white balance processing.

Although other configurations are almost the same as those in the endoscope system according to the second embodiment shown in FIG. 6, the first identifier 22 is used only for determination of the presence or absence of the connection of the camera head 20 and not used for determination of the type of the camera head 20 in the present embodiment. Therefore, the first identifier detection section 38 is not provided in the camera head connection detection section 36.

Next, FIG. 11 is a flowchart showing the working of the endoscope system. Note that the processing steps shown in FIG. 11 are performed based on the control by the control section 37. In addition, in FIG. 11, illustration of control other than the control related to the enhancement processing and the moiré elimination processing (note that the control of the white balance processing relates to the moiré elimination processing in the present embodiment) is omitted for simplification.

Upon starting the processing procedure, the control section performs the processing in the above-described step S1, to wait for the connection of the camera head 20, and then performs the processing in the step S2, to set the enhancement processing to off.

Subsequently, the control section waits until the operation for starting the white balance processing is performed through the camera head operation section 23 or the video processor operation section 39 (step S21). This white balance processing is performed first at the start of usage of the endoscope system. During waiting for the start of the white balance processing, indication for urging the performance of the white balance processing may be displayed on the monitor 50.

When the operation for starting the white balance processing is performed, an image of a white object (white plate or white cloth, for example) is picked up to obtain a video signal, and white balance processing is performed such that the white balance of the obtained video signal falls within a predetermined range indicating white color (step S22).

The video signal obtained for the white balance processing is further inputted to the moiré elimination section 34, and features of the moiré (wavelength and intensity of the moiré) are detected based on the cycle and amplitude of the magnitude of the signal value (magnitude of the luminance value) (step S23).

Then, the control section 37 selects the moiré elimination filter that effectively eliminates the detected features of the moiré (for example, the moiré elimination filter having the center band of the moiré elimination band which is closest to the detected wavelength of the moiré, having the moiré elimination band in which all the wavelengths, if possible, are included when moiré having a plurality of wavelengths occurs, and having a reducing level of the signal value which corresponds to the intensity of the moiré), to set the moiré elimination filter for the moiré elimination section 34 (step S24). However, for the practical purposes, the control section 37 previously includes a table or the like that indicates which moiré elimination filter is applied to which case, i.e., which wavelength range the wavelength of the moiré falls within and which intensity range the intensity of the moiré falls within, and sets the moiré elimination filter with reference to the table.

After that, the control section 37 causes the moiré elimination section 34 to perform the moiré elimination processing in the step S3 according to the moire elimination processing automatically set in the step S24, to terminate the processing procedure.

According to the fourth embodiment thus configured, it is possible to provide almost the same effects as those in the above-described first to third embodiments. In addition, in the present embodiment, the features of the moiré are automatically detected based on the video signal, and appropriate moiré processing is performed. Such configuration enables the moiré which actually occurs to be eliminated more efficiently.

In addition, the white balance processing that has been widely performed at the time of using endoscope systems is focused on, and the features of the moiré are detected by using the video signal obtained for the white balance processing, which eliminates the need for separately obtaining a video signal for detecting the features of the moiré. As a result, it is possible to facilitate the operation and enhance the efficiency of endoscopic examinations.

Note that, in the above-described embodiments, description has been made on the configuration in which the optical image transmitted by the image guide fiber bundle 13 of the optical endoscope 10 is picked up by the image pickup device 21 of the camera head 20, and the generated video signal is outputted from the video signal output section 28 in the camera head 20 to the video signal reception section 29 in the video processor 30. However, the present invention is not limited to such a configuration. For example, the present invention can be similarly applied to, what is called, a hybrid scope, that is, a scope of a type in which the transmission of an optical image from the distal end to the proximal end of the insertion portion is performed through the image guide fiber bundle 13, and the transmitted optical image is picked up by the image pickup device 21 provided at the proximal end portion of the insertion portion. In this case, the hybrid scope is configured to include the video signal output section 28. Even in such a configuration, when the optical image transmitted by the image guide fiber bundle 13 is picked up by the image pickup device 21, an image in which moiré is eliminated can be observed without a need for performing complicated operation.

Description has been mainly made above on the endoscope system. However, the present invention may be an actuation method of the endoscope system for actuating the endoscope system as described above, a processing program for causing a computer to actuate the endoscope system as described above, a non-transitory computer-readable recording medium that records the processing program, or the like.

The present invention is not limited to the above-described embodiments as they are, and can be embodied by modifying the constituent elements within a range not departing from the gist of the invention in practical stages.

In addition, various aspects of the invention can be formed by appropriately combining a plurality of constituent elements disclosed in the above-described embodiments. For example, some constituent elements can be deleted from all of the constituent elements shown in the embodiments. Furthermore, constituent elements in different embodiments can be appropriately combined. Thus, it is needless to say that various modifications and applications can be possible without departing from the gist of the invention.

What is claimed is:
1. An endoscope system comprising:
an optical endoscope including:
an insertion portion configured to be inserted into a subject;
an objective optical system provided at a distal end portion of the insertion portion; and
an image guide fiber bundle that transmits an optical image formed by the objective optical system from the distal end portion to a rear end portion of the insertion portion;
a camera head configured to be attachable to and detachable from the optical endoscope and including an image pickup device that picks up the optical image transmitted by the image guide fiber bundle and generates a video signal;
a video signal output section that is provided in the camera head and outputs the video signal generated by the image pickup device;
a video processor that is configured such that the camera head is attachable to and detachable from, and processes the video signal;
a video signal reception section that is provided in the video processor and receives the video signal outputted from the video signal output section;
a moiré elimination section that is provided in the video processor and performs moiré elimination processing for eliminating moiré included in the video signal received by the video signal reception section, by means of image processing;
a control section that is provided in the video processor and causes the moire elimination section to perform the moiré elimination processing; and
an enhancement processing section that is provided in the video processor and performs image enhancement on the video signal,
wherein the moiré elimination section is configured as a result that a filter coefficient to be used when the enhancement processing section performs image enhancement is replaced with a filter coefficient for moiré elimination, and the moire elimination section uses a processing circuit of the enhancement processing section as a processing circuit of the moiré elimination section itself,
the camera head further includes a first identifier for identifying a type of the camera head,
the video processor includes a first identifier detection section that detects the first identifier of the camera head connected to the video processor, and
the control section causes the moiré elimination section to perform the moire elimination processing corresponding to a detection result of the first identifier.
2. The endoscope system according to claim 1, wherein the optical endoscope further includes a second identifier for identifying a type of the optical endoscope,
the video processor further includes a second identifier detection section for detecting the second identifier, and the control section causes the moiré elimination section to perform the moire elimination processing corresponding to the detection result of the first identifier and a detection result of the second identifier.

3. The endoscope system according to claim 2, wherein the control section sets the moiré elimination processing in which a wavelength of the moiré is included in an elimination band, according to the detection result of the first identifier and the detection result of the second identifier, and causes the moiré elimination section to perform the set moiré elimination processing.

4. The endoscope system according to claim 1, further comprising
an operation section that is capable of performing selection operation of the moiré elimination processing, wherein
when the selection operation of the moiré elimination processing is performed through the operation section, the control section prioritizes the selected moire elimination processing over the moiré elimination processing corresponding to the detection result of the first identifier, and causes the moiré elimination section to perform the prioritized moiré elimination processing.

5. An endoscope system comprising:
an optical endoscope including:
 an insertion portion configured to be inserted into a subject;
 an objective optical system provided at a distal end portion of the insertion portion; and
 an image guide fiber bundle that transmits an optical image formed by the objective optical system from the distal end portion to a rear end portion of the insertion portion;
a camera head configured to be attachable to and detachable from the optical endoscope and including an image pickup device that picks up the optical image transmitted by the image guide fiber bundle and generates a video signal;
a video signal output section that is provided in the camera head and outputs the video signal generated by the image pickup device;
a video processor that is configured such that the camera head is attachable to and detachable from, and processes the video signal;
a video signal reception section that is provided in the video processor and receives the video signal outputted from the video signal output section;
a moiré elimination section that is provided in the video processor and performs moiré elimination processing for eliminating moiré included in the video signal received by the video signal reception section, by means of image processing;
a control section that is provided in the video processor and causes the moire elimination section to perform the moiré elimination processing; and
an enhancement processing section that is provided in the video processor and performs image enhancement on the video signal,
wherein the video processor further includes a white balance processing section that performs white balance processing on the video signal,
the moiré elimination section is configured as a result that a filter coefficient to be used when the enhancement processing section performs image enhancement is replaced with a filter coefficient for moiré elimination, and the moiré elimination section uses a processing circuit of the enhancement processing section as a processing circuit of the moiré elimination section itself and detects a wavelength of the moire based on the video signal obtained for the white balance processing, and
the control section sets the moiré elimination processing in which the detected wavelength of the moiré is included in an elimination band, and causes the moire elimination section to perform the set moiré elimination processing.

* * * * *